United States Patent [19]

Sakuma et al.

[11] Patent Number: 4,704,274
[45] Date of Patent: Nov. 3, 1987

[54] METHOD FOR THE PURIFICATION OF LPF-HA

[75] Inventors: Shin Sakuma; Kuniaki Sakamoto; Hisashi Kitagawa; Mitsuo Sakoh; Saneo Nonaka, all of Kumamoto, Japan

[73] Assignee: Juridical Foundation The Chemo-Sero-Therapeutic Research Institute, Kumamoto, Japan

[21] Appl. No.: 666,172

[22] Filed: Oct. 26, 1984

[30] Foreign Application Priority Data

Nov. 1, 1983 [JP] Japan .................................. 58-206598

[51] Int. Cl.$^4$ .......................... A61K 39/02; C07K 3/20
[52] U.S. Cl. ...................................... 424/88; 424/92; 435/68; 435/70; 435/822; 530/413
[58] Field of Search ...................... 424/88, 92; 435/68; 530/413

[56] References Cited

U.S. PATENT DOCUMENTS 4,247,452  1/1981  Irons et al. ...................... 260/112 B
4,551,429  11/1985  Greenspan ............................ 424/92
4,563,303  1/1986  Gennaga et al. ...................... 424/92

FOREIGN PATENT DOCUMENTS 0035204  9/1981  European Pat. Off. .
57-2688  1/1982  Japan .

OTHER PUBLICATIONS

Science, 127, 1963, p. 588, Morell et al.
Infect and Immunity, 41(1), 1983, pp. 313–320, Sato et al.
Infect and Immunity, 39(2), 1983, pp. 590–598, Robinson et al.
C. A., vol. 96, 1982, #197728e, Cowell et al.

Primary Examiner—John Kight
Assistant Examiner—Garnette D. Draper
Attorney, Agent, or Firm—Wegner & Bretschneider

[57] ABSTRACT

A method for producing highly pure LPF-HA (Leucocytosis-promoting Factor Hemagglutinin) from culture media of Bordetella pertussis in a high yield by an affinity chromatography using a denatured ceruloplasmin as a ligand. The LPF-HA obtained by this invention is highly pure and does not contain almost endotoxin of B. pertussis and is useful for the preparation of various reagents utilizing the physiological activities, a medicine for treating diabetes, and a pertussis vaccine.

8 Claims, No Drawings

METHOD FOR THE PURIFICATION OF LPF-HA

The present invention relates to a method for the purification of LPF-HA. More paticularly, it relates to a method for producing LPF-HA (Leucocytosis-promoting Factor Hemagglutinin) from culture media of *Bordetella pertussis* in a high yield and high purity by an affinity chromatography using a denatured ceruloplasmin as a ligand.

TECHNICAL FIELD

LPF-HA is an active substance produced by *B. pertussis* phase I and phase II strains which is not produced by *B. pertussis* phase III strain having no virulence or *Bordetella parapertussis*, *Bordetella bronchiseptica*. The LPF-HA is also called as *B. pertussis* toxin and is a protein having various physiological activities. The main physiological activities are a leucocytosis-promoting activity, an insulin secretion-enhancing activity, a histamine-sensitizing activity, a hemagglutinating activity, and the like. Particularly, because of the insulin secretion-enhancing activity, it is noticed that the LPF-HA may be useful for the treatment of diabetes.

Separately from the above physiological activities, it has recently been noticed that LPF-HA shows an important function in the prophylaxis of infection of *B. pertussis* and infectious disease thereof and hence is useful as an antigen for prophylaxis of infection of *B. pertussis* [cf. Pittman, M.; Review of Infectious Diseases, 1, 401– 409 (1979), and Sato, Y. et al.; Seminars in Infectious Diseases IV, Bacterial Vaccine, 380–385 (1982)].

Thus, it has been desired to develop an improved method for the separation and purification of LPF-HA simply and in a large quantity, for the purpose of studying the physiological activities of LPF-HA, of producing a medicine and of producing a pertussis vaccine having less side effect in an industrial scale.

PRIOR ART

According to known methods, the separation and purification of LPF-HA is carried out by salting out a culture medium of *B. pertussis* with ammonium sulfate, extracting and dialyzing, and then subjecting the thus obtained material to ion exchange chromatography, gel filtration [cf. Arai, H.; Biochimica et Biophysica Acta, 444, 765 (1976)] or to sucrose concentration gradient centrifugation [cf. Sato, Y.; Infect. Immun., 6, 897–704 (1972)]. According to such known methods, however, it is very hard to obtain the desired LPF-HA which shows single band in the purification analysis by electrophoresis, and its yield is very low.

In order to obtain the desired highly pure LPF-HA in a comparatively large amount, it is also proposed that a supernatant of culture media of *B. pertussis* is passed through a column packed with hydroxyapatite to adsorb LPF-HA thereon, followed by washing, eluting and then subjecting to affinity chromatography with concanavalin A-Sepharose (Con A-Sepharose, manufactured by Pharmacia) [cf. Yajima, M.et al.; J. Biochem., 83, 295–303 (1978)]. However, the affinity chromatography using concanavalin A as a ligand not only has an affinity with LPF-HA but also can adsorb saccharides, glycolipids and also other glycoproteins, and hence, it adsorbs other pertussis cell components such as F-HA (Filamentous-Hemagglutinin) and cell membrane components, which results in difficulty of isolation of the desired highly pure LPF-HA. Thus, it is not suitable as an affinity chromatography for LPF-HA.

Since it has recently been found that human haptoglobin binds specifically to LPF-HA, it has been tried to purify LPF-HA by an affinity chromatography using as a ligand the human haptoglobin instead of the above concanavalin [cf. Iron, L. et al.; Biochimica et Biophisica Acta, 580, 175–185 (1979), and Cowell, J. et al.; Seminars in Infectious Diseases IV, Bacterial Vaccine, 371–379 (1982)]. In this case of using human haptoglobin as a ligand, there newly occurs other problem that it is necessary to take a measurement against hepatitis virus. That is, since the human haptoglobin is collected from human blood, it may be contaminated with hepatitis virus and further other unknown infectious factors. This problem is also included in case of using other animal blood. Unfortunately, however, there is no method for surely checking the contamination with hepatitis virus. It is also known that the hepatitis virus can be inactivated by heating it at 60° C. for 10 to 15 hours. It has been found by the present inventors that when haptoglobin is subjected to such a heat treatment, it looses almost the affinity to LPF-HA and hence can not exhibit the desired effect when used in the affinity chromatography.

Moreover, in case of the purification using hydroxyapatite as mentioned above, it takes a long period of time in the treatment with a column packed with hydroxyapatite, and hence, it may result in lowering of activity of LPF-HA. Thus, this method is not suitable for the purification of LPF-HA in a low cost and in an industrial scale, either.

Recently, there has also been proposed a method for collecting LPF-HA which comprises fracturing mechanically *B. pertussis* cells, extracting LPF-HA from the cell components, subjecting it to ammonium sulfate fractionation, and then, subjecting the thus obtained material to affinity chromatography using as a ligand plasma sialoproteins such as haptoglobin or ceruloplasmin, or sialoproteins such as salivary mucin (cf. British Patent First Publication 2,015,531). However, the ligand specifically disclosed in this British patent publication is merely human haptoglobin, and hence, this method still includes the problem of necessity of taking measurement for the hepatitis virus as mentioned above. Besides, the above British patent publication does not specifically mention ceruloplasmin, and it is unclear therefrom that it is effective or not. As a result of the present inventors' study, when ceruloplasmin is used as it stands, it can not exhibit suffifient effect for purification of LPF-HA.

OBJECTS OF THE INVENTION

Based on the above technical situation, the present inventors have intensively studied on an improved method for isolation and purification of LPF-HA in an industrial scale. As a result, it has been found that when a denatured ceruloplasmin is used as a ligand in an affinity chromatography, the desired purification of LPF-HA can be achieved, and further that even when it is heat-treated at 60° C. for 10 to 15 hours in order to eliminate hepatitis virus, etc., it does not lower its adsorbability of LPF-HA but rather shows increased adsorbability.

The main object of the present invention is to provide an improved method for obtaining *B. pertussis* LPF-HA in a high yield and high purity in a single step, wherein the collection of LPF-HA from culture media of *B.*

*pertussis* is carried out by an affinity chromatography using a denatured ceruloplasmin as a ligand. Another object of the invention is to provide a highly pure LPF-HA having no contamination with hipatitis virus or other infectious factors owing to the ligand used in the affinity chromatography. These and other objects and advantages of the present invention will be apparent to persons skilled in the art from the following description.

DETAILED EXPLANATION OF THE INVENTION

The method for the purification of LPF-HA according to the present invention is characteristic in that the starting culture medium obtained by culturing *B. pertussis* in a usual manner is subjected to an affinity chromatography using a denatured ceruloplasmin as a ligand, whereby the endotoxins of *B. pertussis* are separated out during the purification of LPF-HA to give a highly purified LPF-HA in a high yield.

The starting culture media of *B. pertussis* include culture media obtained by culturing *B. pertussis* phase I (or phase II) strain in a conventional liquid medium, such as Cohen-Wheeler medium or Stainer-Scholte medium, in a usual manner, such as stationary culture or tank culture. Preferably, the culture media are subjected to centrifugation or filtration in order to remove cells. According to the method of the present invention, the culture media can be applied to the affinity chromatography as they stand, i.e. without subjecting to various pre-treatments such as salting out, extraction, dialysis, ultracentrifugation, concentration, equilibration, or the like, and hence, the procedure is very simple.

The denatured ceruloplasmin used in the present invention are obtained by denaturing ceruloplasmin origined from animals by various methods, for example, by heating ceruloplasmin at 60° to 85° C. for 1 to 24 hours, or by treating ceruloplasmin with a denaturing agent, such as a sulfide (e.g. sodium sulfide, ammonium sulfide, etc.), a reducing sugar (e.g. L-ascorbic acid, D-glucose, D-fructose, maltose, lactose, etc.), a reducing agent (e.g. acetaldehyde, formic acid, oxalic acid, mercaptoethanol, diethyldithiocarbamate, etc.), a cyano compound (e.g. sodium cyanide, sodium thiocyanate, etc.), a chelating agent (e.g. EDTA, nitrotriacetic acid (NTA), triethylenetetraminehexaacetic acid (TTHA), etc.), whereby the copper ion ($Cu^{++}$) contained in ceruloplasmin is reduced or a part or whole of the copper ion is isolated and removed.

The above denaturing means may be applied to alone or in combination of two or more, and the denaturing may be applied to after immobilizing ceruloplasmin (i.e, a ligand) into the matrix (i.e. a suppoting carrier). The denaturing can easily be carried out by dialyzing one volume of a 0.1 to 0.5 w/v % solution of ceruloplasmin in physiological saline solution against 10 to 200 volume of the following buffer. That is, in case of using sodium sulfide, ammonium sulfide, or sodium cyanide as the denaturing agent, a 0.01 to 0.1 M phosphate buffer containing 0.01 to 1.0 M of the denaturing agent (pH 4.0–6.0) is used, and the dialysis is carried out at 0° to 60° C. for 1 to 10 hours. In case of using L-ascorbic acid or ruducing sugars as the denaturing agent, a 0.01 to 0.1 M acetate buffer containing 0.01 to 1.0 M of the denaturing agent (pH 4.0–6.0) is used, and the dialysis is carried out at 0° to 15° C. for 24 to 36 hours. In case of using acetaldehyde, formic acid, oxalic acid, mercaptoethanol, diethyldithiocarbamate, or the like as the denaturing agent, a 0.01 to 0.1 M phosphate buffer containing 0.01 to 0.1 M of the denaturing agent (pH 6.0–8.0) is used, and the dialysis is carried out at 0° to 30° C. for 0.5 to 3 hours. In case of using thiocyanates as the denaturing agent, 0.01 to 0.1 M phosphate buffer containing 0.1 to 3.0 M of the denaturing agent (pH 6.0–8.0) is used, and the dialysis is carried out at 0° to 30° C. for 0.5 to 5.0 hours. In case of using EDTA, NTA, TTHA as the denaturing agent, a 0.01 to 0.1 M phosphate buffer containing 0.01 to 1.0 M of the denaturing agent (pH 6.0–8.0) is used, and the dialysis is carried out at 0° to 30° C. for 0.5 to 5.0 hours.

The starting ceruloplasmin is commercially available, or may be obtained by subjecting blood plasma to alcohol fractionation by Cohn method as Fraction IV, or may be obtained by separating from human or other animals blood and theh purifying.

The affinity chromatography of culture media of *B. pertussis* with the above denatured ceruloplasmin is usually carried out at a pH range of 4.0 to 10.0 in the following manner.

An affinity gel is prepared by the method of Axe'n et al [cf. Axe'n; Nature, 214, 1302–1304 (1967)], i.e. by immobilizing the denatured ceruloplasmin into a matrix of cepharose, agarose, cellulose, or dextran, etc. which are activated with cyano bromide. The affinity gel is contacted with the culture media of *B. pertussis* in column method or batch system, whereby LPF-HA contained in the media is adsorbed onto the gel, followed by washing the gel with an appropriate buffer to remove contaminants and then eluting LPF-HA with an eluent.

According to a column method, the affinity gel is packed into a column, and the starting culture medium of *B. pertussis* is passed through the column at a flow rate of 10 ml/cm$^2$/hour to 500 ml/cm$^2$/hour.

According to a batch method, the culture medium of *B. pertussis* is entered into a vessel, and thereto is directly added the affinity gel, and the mixture is stirred for about 30 minutes to about 3 hours, preferably for about one hour.

The amount of the affinity gel is not critical, but usually, 1 ml of affinity gel is used for absorbing 1,000 to 2,000 g of LPF-HA (in protein amount).

Washing of the LPF-HA-absorbed affinity gel is usually carried out with a buffer having a pH 4.0–9.0, and a specific electric conductivity of 10 ms/cm to 150 ms/cm. For example, by using a 0.01 to 0.1 M phosphate buffer (pH 6.0–8.0) containing 0.1 to 1.0 M sodium chloride, the washing is carried out by flowing the buffer in a volume of several tens times as much as the volume of the column in case of the column method, or by treating with the buffer in a volume of several times as much as the volume of gel in the batch method. By the washing, endotoxin of *B. pertussis* contained in the starting material is effectively removed. This is also one of the characteristics of the present invention, which is superior to the conventional purification methods.

After the above washing step, the LPF-HA adsorbed onto the ligand is eluted in a usual manner by using conventional eluents, such as chaotropic salts (e.g. salts which can release chaotropic ions such as $I^-$, $ClO_4^-$, $CF_3COO^-$, $SCN^-$, $CCl_3COO^-$, etc.), ethylene glycol, dioxane, urea, guanidine hydrochloride, EDTA, or the like.

According to the affinity chromatograpy of the present invention, the desired product can be obtained in a high yield such as more than 90% in case of the starting material having a pH 4.0 to 10.0.

The LPF-HA obtained by the present invention has a high purity as more than 90%, occasionally more than 95% (in the analysis by electrophoresis) as is shown in Table 1. Besides, the product of the present invention has a specific activity of 135–160 (ELISA unit/mg of protein), which can not be achieved by the conventional purification methods.

On the contrary, when the purification is carried out by using a gel containing haptogrobulin as the ligand or a gel containing natural ceruloplasmin as the ligand, the product has poor purity, e.g. less than 85%, and a specific activity of up to 120–130 (ELISA unit/mg of protein). Thus, it is clear that the specific gel of the present invention shows greatly superior specific adsorbability of LPF-HA in comparison with other known gels. Superiority of the present invention is also clear from the results in biological activities tests of the LPF-HA product, such as Limurus test and pyrogen test in rabbit as shown hereinafter. That is, in case of LPF-HA purified by using a gel containing haptoglobin as the ligand, the endotoxin of *B. pertussis* is not sufficiently removed, and hence, the product shows about 1° C. of exotherm, but on the contrary, in the product obtained by the present invention, the undesirable endotoxin is almost completely removed.

Besides, when a haptoglobin is subjected to heat treatment at 60° C. for 10 hours in order to remove hepatitis virus and other infectious factors and the heat-treated haptoglobin is used as a ligand for gel, the gel can entirely not adsorb LPF-HA, and hence, can not be used for the purification of LPF-HA.

According to the present invention, in case of using a ceruloplasmin denatured by heat treatment, the specific adsorbability of LPF-HA and capacity of the adsorption are significantly enhanced, and further, the hepatitis virus or the like is effectively removed. In case of using as the ligand a ceruloplasmin denatured by 1-ascorbic acid, sodium cyanide etc., even if the denatured ceruloplasmin is heat-treated at 60° C. for 10–15 hours, the gel can show sufficient purification capacity as like as the product not subjected to the heat treatment. Besides, even when a ceruloplasmin subjected to heat treatment at 60° C. for 10 hours is further treated with a denaturing agent (e.g. 1-ascorbic acid or sodium cyanide), the denatured product can show the same or more properties as the product denatured with the denaturing agent without subjecting to the heat treatment. Thus, the present invention is far superior to the method using the known gel comprising as a ligand haptoglobin in terms of no danger of contamination of hepatitis virus or the like and further sufficient removal of endotoxin of *B. pertussis.*

The affinity chromatography of the present invention wherein a denatured ceruloplasmin is used as the ligand can give the desired LPF-HA in a high yield and high purity from the starting culture medium of *B. pertussis* by a simple procedure. Besides, the affinity gel can repeatedly be used for several tens of times or more, which is advantageous in view of low cost. The method of the present invention is also advantageous in that endotoxin of *B. pertussis* can almost be removed. Accordingly, the present invention is very useful as an industrial method for obtaining a highly pure LPF-HA.

The LPF-HA obtained by the present invention is highly pure and does not contain other proteins, lipids and saccharides as well as endotoxin, and hence, is useful for the preparation of various reagents utilizing the physiological activities, a medicine for treating diabetes, and a pertussis vaccine.

The present invention is illustrated by the following Preparations, Examples and Experiments, but should not be construed to be limited thereto.

PREPARATION 1

Preparation of human ceruloplasmin:

Cohn's Fraction IV-1 obtained by alcohol fraction of human plasma is used as the starting material. The starting material is subjected to the purification method of Morell et al. [cf. J. Biol. Chem., 244, 3494 (1967)] to separate human ceruloplasmin.

That is, the Cohn's Fraction IV-1 is subjected to an ion exchange chromatography with DEAE-Sepharose CL-6B, and it is subjected to an affinity chromatography with a hemoglobin-Sepharose gel in order to remove the possible contamination of haptoglobin. Thereafter, the solution is salted out with ammonium sulfate and then dialyzed against 0.025 M acetate buffer (pH 5.25) to obtain crystalline human ceruloplasmin.

PREPARATION 2

Preparation of denatured ceruloplasmin:

The crystalline ceruloplasmin obtained in Preparation 1 is denatured in a similar manner to the procedure described in Morell et al., Science, 127, 588 (1963) to prepare various denatured ceruloplasmins.

(1) Ceruloplasmin denatured with sodium cyanide:

A 1 w/v % aqueous solution of crystalline ceruloplasmin (50 ml) is dialyzed against a phosphate buffer (pH 7.4, ionic strength: 0.2) containing 0.05 M sodium cyanide (5.0 liters) at 4° C. for 12 hours to give a sodium cyanidedenatured ceruloplasmin which looses 90% of oxidase activity.

(2) Heat treatment of sodium cyanide-denatured ceruloplasmin:

A 1 w/v % aqueous solution of sodium cyanide-denatured ceruloplasmin is prepared in the same manner as described in the above (1). The solution (50 ml) is dialyzed against 0.1 M phosphate buffer (pH 7.4) (5.0 liters). After the dialysis, the denatured ceruloplasmin-containing solution is heated at 60° C. for 10 hours.

(3) Ceruloplasmin denatured with L-ascorbic acid:

A 1 w/v % aqueous solution of crystalline ceruloplasmin is dialyzed against an acetate buffer (pH 5.2, ionic strength: 1.2) (5.0 liters) containing L-ascorbic acid (5 mg/ml) at 4° C. for 36 hours to give an L-ascorbic acid-denatured ceruloplasmin which show 65.5% oxidase activity.

(4) Ceruloplasmin denatured by heat treatment:

A 0.1 M phosphate buffer (pH 7.5) (100 ml) containing 5 w/v % of a crystalline ceruloplasmin is heat-treated at 60° C. for 15 hours.

PREPARATION 3

Heat-treated ceruloplasmin denatured with L-ascorbic acid:

Cohn's Fraction IV-1 obtained by alcoholic fractionation of human plasma is heated on a bath at 60° C. for 10 hours. The solution is treated in the same manner as described in Preparation 1 to give a heat-treated crystalline cruloplasmin.

The heat-treated crystalline ceruloplasmin thus obtained is treated in the same manner as described in Preparation 2-(3) to give a heat-treated ceruloplasmin denatured with L-ascorbic acid.

PREPARATION 4

Preparation of affinity gel:

The above crystalline ceruloplasmin and various denatured ceruloplasmins (as a ligand) are subjected to coupling reaction with CNBr-activated Sepharose 4B (manufactured by Pharmacia) to prepare affinity gels in the following manner.

CNBr-activated Sepharose 4B (1.5 g) is swollen by dipping in 1.0 mM hydrochloric acid (3.0 liters) for 15 minutes, and then 1.0 mM hydrochloric acid is removed by suction on a glass filter (3 G) to give a swollen Sepharose gel (5.25 ml).

Separately, a ligand (protein amount: 150 mg) is dissolved in 0.1 M sodium carbonate buffer (pH 8.3, 75 ml ) containing 0.5 M sodium chloride, and thereto is added the above-prepared swollen Sepharose gel (5.25 ml). The mixture is gently stirred at room temperature for 2 hours to complete the coupling reaction. After the coupling reaction, the reaction mixture is washed with the same sodium carbonate buffer as above (150 ml) four times, and thereto is added 1.0 M ethanolamine (pH 8.0, 150 ml), and the mixture is again reacted with gently stirring for 2 hours. After completion of the reaction, the reaction mixture is washed with the same sodium carbonate buffer (150 ml) four times to remove ethanolamine. The resulting gel is washed with 0.1 M acetate buffer (pH 8.0) containing 1.0 M sodium chloride (150 ml) three times, and further with 0.1 M borate buffer (pH 8.0) containing 1.0 M sodium chloride (150 ml) three times. The washing with the acetate buffer and the borate buffer are mutually repeated each three times to give ceruloplasmin-Sepharose affinity gel and denatured ceruloplasmin-Sepharose affinity gels.

EXAMPLE 1

Purification of LPF-HA by column method:

The affinity gel (20 ml) prepared in the above Preparation 3 is packed in a column (28 mm$\phi$ × 150 mm$\phi$), and a supernatant of a culture medium of *B. pertussis* (5.0 liters) containing LPF-HA of 1,400 ELISA unit/ml is passed through the column at room temperature at a flow rate of 150 ml/cm$^2$/hour Thereafter, a 0.1 M phosphate buffer (pH 7.0, specific electric conductivity: 100 ms/cm, 1,500 ml) containing 1.0 M sodium chloride is passed through the column at the same flow rate as above to wash the column.

After the washing, an eluent (100 ml) consisting of 0.1 M phosphate buffer (pH 7.5) containing 1.0 M sodium chloride and 3.0 M sodium thiocyanate is passed through the column at a flow rate of 35.0 ml/cm$^2$/hour in order to elute LPF-HA.

There are disclosed in Table 1 the analytical data of the LPF-HA fraction and experimental data in the cases of using affinity gels wherein the denatured ceruloplasmins and undenatured ceruloplasmin and haptoglobin (as the references) are used as the ligand.

As is clear from the resuls, in case of using various denatured ceruloplasmins of the present invention as the ligand, the LPF-HA obtained has a high purity and a high specific acitivity. On the contrary, in case of using undenatured ceruloplasmin as the ligand, the product is a low purity and low specific activity and is obtained in a very low yield. Besides, in case of using known haptoglobin as the ligand, the product is less inferior quality with less yield. Moreover, when a haptoglobin heat-treated at 60° C. for 10 hours is used as the ligand, LPF-HA is entirely not adsorbed.

The gel of haptoglobin (ligand) used as the reference is prepared by coupling a commercially available haptoglobin with CNBr-activated Sepharose 4B in the same manner as described in the above Preparation 4.

TABLE 1

| Kind of ligand for affinity gel | Amount of eluent (ml) | LPF—HA activity[1] × 10$^4$ unit/ml | HA value | Specific activity[2] | Purity[3] (%) | Yield (%) |
|---|---|---|---|---|---|---|
| NaCN—denatured ceruloplasmin [Prepn. 2-(1)] | 100 | 6.46 | 512 | 137.7 | 92.3 | 92.3 |
| NaCN—denatured, heat-treated ceruloplamin [Prepn. 2-(2)] | 100 | 6.50 | 512 | 141.6 | 93.0 | 92.9 |
| l-Ascorbic acid-denatured ceruloplasmin [Prepn. 2-(3)] | 100 | 6.58 | 1024 | 138.2 | 93.1 | 94.0 |
| Heat treated ceruloplasmin [Prepn. 2-(4)] | 100 | 6.44 | 512 | 150.0 | 94.6 | 92.0 |
| Heat treated, l-ascorbic acid-denatured ceruloplasmin [Prepn. 3] | 100 | 6.94 | 512 | 159.5 | 95.3 | 99.1 |
| Undendatured ceruloplasmin [Prepn. 1] | 100 | 5.46 | 512 | 126.7 | 88.8 | 78.0 |
| Haptoglobin | 100 | 4.50 | 256 | 123.1 | 82.7 | 64.3 |
| Heat treated haptoglobin | 100 | 0 | 0 | 0 | 0 | 0 |

[1]Measured by ELISA analysis [cf. Sato et al., Symposium on Toxins, proceeding of the 28th symposium on Toxins, 141–144 (1981)]
[2]LPF—HA activity (ELISA unit/ml)/protein content ($\mu$g/ml)
[3]Measured by polyacrylamide gel electrophoresis - analysis with densitometer

EXAMPLE 2

Purification of LPF-HA by batch method:

Into a 5 liter wide neck flask is charged a supernatant (4.0 liters) of a culture medium of *B. pertussis* containing LPF-HA (1,400 ELISA unit/ml), and thereto is directly added an affinity gel (20 ml). The mixture is mildly stirred at room temperature for 1 hour to adsorb LPF-HA onto the affinity gel, and thereafter, the supernatant of a culture medium is removed by suction with a glass filter (G2). The gel remained on the glass filter is washed with 0.1 M phosphate buffer (pH 7.5, specific electric conductivity: 100 ms/cm) containing 1.0 M sodium chloride (300 ml) and a phosphate buffer (pH 8.0, specific electric conductivity: 100 ms/cm) containing 1.0 M sodium chloride (300 ml). The washings are mutually repeated three times.

After the washing, LPF-HA is eluted from the gel in the following manner. That is, onto the gel remained on the glass filter is poured an eluent (50 ml) consisting of 0.1 M phosphate butter (pH 7.5) containing 1.0 M sodium chloride and 3.0 M sodium thiocyanate. After maintaining for 5 minutes, the gel is sucked to elute LPF-HA. The eluted LPF-HA is dialyzed against 0.01 M phosphate buffer (pH 7.5) to remove sodium thiocyanate. The LPF-HA thus obtained is analyzed in the same manner as in Example 1.

The LPF-HA is subjected to Limurus test to measure the endotoxin of B. pertussis and further to the measurement of leucocytosis-promoting activity in mice and other physiological activities. These results are shown in Table 2 and Table 3.

As is clear from the results, in case of using a gel of the denatured ceruloplasmin (as a ligand) of the present invention, a highly pure LPF-HA is obtained in a high yield and the endotoxin of B. pertussis is almost removed (see Limurus test). On the contrary, in case of the reference gel of haptoglobin (as a ligand), the endotoxin is insufficiently removed. The LPF-HAs thus obtained are subjected to pyrogen test in rabbits. As a result, the LPF-HAs purified by the gels of the denatured ceruloplasmins (as a ligand) of the present invention are all negative, which means that the endotoxin is sufficiently removed.

TABLE 2

| Kind of ligand for affinity gel | Amount of eluent (ml) | LPF—HA activity × $10^4$ unit/ml | HA value | Specific activity | Purity (%) | Yield (%) | Limurus test (W) |
|---|---|---|---|---|---|---|---|
| NaCN—denatured ceruloplasmin | 50 | 11.1 | 1024 | 157.4 | 92.5 | 99.1 | 100 |
| l-Ascorbic acid-denatured celuroplasmin | 50 | 11.7 | 1024 | 169.6 | 96.8 | 104.5 | 100 |
| Heat treated ceruloplasmin | 50 | 11.4 | 1024 | 155.5 | 92.6 | 101.8 | 100 |
| Haptoglobin | 50 | 7.8 | 512 | 125.0 | 80.5 | 70.3 | 100 |

[Note]:
The starting supernatant of a culture medium has an endotoxin content of $1.0 \times 10^5$ W by Limurus test.

TABLE 3

| Kind of ligand for affinity gel | Leucocytosis-promoting activity in mice (*1) (LPU/ml) | Histamine-sensitizing activity in mice (*2) (HSU/ml) | $HSD_{50}$ (g) | Pyrogen test in rabbit (°C.) |
|---|---|---|---|---|
| Starting material (Supernatant of culture medium of B. pertussis) | 15.0 | 3.0 | — | 3.5 |
| LPF—HA purified by heat-treated ceruloplasmin gel | 1238.4 | 385.6 | 0.02 | 0.1 |
| LPF—HA purified by haptoglobin | 675.3 | 225.4 | 0.04 | 1.0 |

(*1) and (*2): Minimum Requirement of Biological Products, Ministry of Health and Welfare, Japan, #287, 1981.

What is claimed is:

1. In a method for production of pure LPF-HA (Leucocytosis-promoting factor hemagglutinin) comprising subjecting a culture medium of Bordetella pertussis to an affinity chromatography and eluting LPF-HA adsorbed on the affinity chromatography gel with an eluent, the improvement comprises subjecting the culture medium to an affinity chromatography using a heat-treated ceruloplasmin as a ligand for the affinity chromatography gel.

2. The method according to claim 1, wherein the affinity chromatography is carried out on a culture medium having pH 4.0 to 10.0.

3. The method according to claim 1, wherein the heat-treated ceruloplasim is obtained by heat treatment of a human- or other animal-origin ceruloplasmin at 60° to 85° C. for 1 to 24 hours.

4. The method according to claim 1, wherein the heat-treated ceruloplasmin is obtained by heat-treating a human- or other animal-origin ceruloplasmin and further treating it with a denaturing agent selected from the group consisting of a sulfide, a reducing sugar, a cyano compound, and a chelating agent, whereby copper ion is reduced or a part or all of copper ion is removed.

5. The method according to claim 4, wherein the the denaturing agent is a member selected from the group consisting of sodium sulfide, ammonium sulfide, 1-ascorbic acid, D-glucose, D-fructose, maltose, lactose, acetaldehyde, formic acid, oxalic acid, mercaptoethanol, diethyldithiocarbamate, sodium cyanide, sodium thiocyanate, EDTA, nitrotriacetic acid, and triethylenetetraminehexaacetic acid.

6. The method according to claim 5, wherein the denaturing agent is a member selected from the group consisting of sodium cyanide and 1-ascorbic acid.

7. The method according to claim 1, wherein the affinity chromatography is carried out by a column method comprising passing a culture medium of B. pertussis through a column packed with an affinity chromatography gel using a heat-treated ceruloplasmin as a ligand at a flow rate of 10 to 500 ml/cm²/hour, washing the column with a buffer having a pH 4.0 to 9.0 and a specific electric conductivity of 10 to 150 ms/cm, followed by eluting the adsorbed LPF-HA with an eluent selected from the group consisting of chaotropic base, an ethylene glycol, dioxane, urea, guanidine hydrochloride, and EDTA.

8. The method according to claim 1, wherein the affinity chromatography is carried out by a batch method comprising stirring a mixture of a culture medium of B. pertussis and an affinity chromatograghy gel using a heat-treated ceruloplasmin as a ligand for 30 minutes to 3 hours, washing the mixture with a buffer having a pH 4.0 to 9.0 and a specific electric conductivity of 10 to 150 ms/cm, followed by eluting the adsorbed LPF-HA with an eluent selected from the group consisting of chaotropic base, an ethylene glycol, dioxane, urea, guanidine hydrochloride, and EDTA.

* * * * *